US007361638B2

(12) United States Patent
Berlanga Acosta et al.

(10) Patent No.: US 7,361,638 B2
(45) Date of Patent: Apr. 22, 2008

(54) PHARMACEUTICAL COMBINATION FOR THE TREATMENT OF TISSUE DAMAGE OWING TO AN ARTERIAL IRRIGATION DEFECT

(75) Inventors: Jorge Berlanga Acosta, Habana (CU); Gerardo Enrique Guillen Nieto, Habana (CU); Diana Garcia Del Barco Herrera, Habana (CU); Julio Raul Fernandez Masso, Habana (CU); Mario Pablo Estrada Garcia, Habana (CU); Isabel Guillen Perez, Habana (CU); Jose Suarez Alba, Habana (CU); Rebeca Martinez Rodriguez, Habana (CU)

(73) Assignee: Centro de Ingenieria Genetica y Biotecnologia, Playa Ciudad de la Habana (CU)

( * ) Notice: Subject to any disclaimer, the term of this patent is extended or adjusted under 35 U.S.C. 154(b) by 555 days.

(21) Appl. No.: 10/220,750

(22) PCT Filed: Dec. 17, 2001

(86) PCT No.: PCT/CU01/00013

§ 371 (c)(1),
(2), (4) Date: Apr. 22, 2003

(87) PCT Pub. No.: WO02/053167

PCT Pub. Date: Jul. 11, 2002

(65) Prior Publication Data

US 2003/0186865 A1  Oct. 2, 2003

(30) Foreign Application Priority Data

Jan. 3, 2001  (CU) ................................ 2001/0005

(51) Int. Cl.
*A61K 38/08* (2006.01)
*A61K 38/18* (2006.01)
*C07K 14/485* (2006.01)
*C07K 14/495* (2006.01)

(52) U.S. Cl. .................. 514/17; 514/12; 530/329; 530/300

(58) Field of Classification Search ............ None
See application file for complete search history.

(56) References Cited

U.S. PATENT DOCUMENTS

| 5,360,790 A | 11/1994 | Humes |
| 6,124,263 A * | 9/2000 | Muccioli et al. |
| 6,191,109 B1 | 2/2001 | Besner et al. |
| 6,861,409 B2 * | 3/2005 | Martinez et al. |

FOREIGN PATENT DOCUMENTS

| EP | 0 357 240 A2 | 3/1990 |
| EP | 1 002 802 A1 | 5/2000 |
| KR | 1019970032600 | 7/1997 |
| KR | 100226985 B1 * | 7/1999 |
| WO | WO 98/22124 | 5/1998 |
| WO | WO 00/12047 | 3/2000 |
| WO | WO 01/85695 A1 | 11/2001 |
| WO | WO 01/87322 A2 | 11/2001 |

OTHER PUBLICATIONS

Humes et al., Epidermal growth factor enhances renal tubule cell regeneration and repair and accelerates the recovery of renal function in postischemic acute renal failure, J. Clin. Invest., 84:1757-1761, Dec. 1989.*
Berti et al., Chapter 24: Hexarelin, a synthetic growth hormone secretagogue, exhibits protectant activity in experimental mycardial ischemia and reperfusion, Growth Hormone Secretagogues, E. Ghigo et al., Eds., (Elsevier: Amsterdam), pp. 301-314, 1999.*
Weekers et al., Pretreatment with growth hormone-releasing peptide-2 directly protects against the diastolic dysfunction of mycardial stunning in an isolated, blood-perfused rabbit heart model, Endocrinol., 141(11):3993-3999, 2000.*
Ishikawa et al., Epidermal growth factor protects gastric mucosa against ischemia-reperfusion injury, J. Clin. Gastro., 17 (Sup. 1):S104-S110, 1993.*
Sumi et al., Effect of human epidermal growth factor (hEGF) on splanchnic circulation in dogs, Life Sci., 47 :1115-1119, 1990.*
Lee et al., Effects of epidermal growth factor (EGF) on ischemia-repertusion injury in rat liver, Chung-Ang J. Med., 25(4):195-205, Dec. 2000.*
Bowers et al., Chapter 2: Xenobiotic growth hormone secretagogues: growth hormone releasing peptides, Growth Hormone Secretagogues, B.B. Bercu and R. Walker, Eds., (Springer: New York), pp. 9-28, 1996.*

(Continued)

*Primary Examiner*—Lorraine Spector
*Assistant Examiner*—Claire Kaufman
(74) *Attorney, Agent, or Firm*—Hoffmann & Baron, LLP

(57) ABSTRACT

This invention relates to a medicine for humans, and particularly to a pharmaceutical combination comprising Epidermal Growth Factor (EGF) and Growth Hormone secretagogue hexapeptide (GHRP) for use in preventing tissue damage due to blood flow suppression by enhancing tissue repair following ischemic damage. The aforementioned combination may be applied as a single pharmaceutical composition. Alternatively, an individual may also receive both EGF and GHRP in a separate manner but within a single therapeutic regime to enhance cellular survival when organs are subjected to blood flow deprivation for a critical period of time. This combination attenuates reactive oxygen species (ROS) formation and its associated cytotoxicity. It is also useful in promoting cellular survival when tissue or organs are exposed to prolonged ischemic periods. The combination is useful as a prophylactic agent in those subjects prone to multiple organ failure (MOF) such as burn victims, multiple trauma patients, hypoxic neonates, acute respiratory distress syndrome patients, and necrotizing enterocolitis patients.

7 Claims, No Drawings

OTHER PUBLICATIONS

Muccioli et al., Growth hormone-releasing peptides and the cardiovascular system, Annales d'Endocrinologie, 61(1):27-31, Feg. 2000.*

Locke et al., Intracerebroventricular growth-hormone-releasing peptide-6 stimulates eating without affecting plasma growth hormone responses in rats, Life Sci., 56(16):1347-1352, 1995.*

Hui et al., Effects of epidermal growth factor on gastric blood flow in rats: possible role in mucosal protection, Gastroenterology, 104:1605-1610, 1993.*

BioTech Life Sciences Dictionary, (online) peptide, The Trustees of Indiana University, 1995-1998, accessed Apr. 23, 2007.*

W. Ganong, Reviewof Medical Physiology, 17$^{th}$ Ed., Appleton & Lange:Norwalk, CT, 1995, p. 268.*

Halle et al., Importance of TNF-alpha and leptin in obesity and insulin resistance: a hypothesis on the impact of physical exercise, Exercise Immunology Review, 4:77-94, 1998.*

Svensson et al., The GH secretagogues ipamorelin and GH-releasing peptide-6 increased bone mineral content in adult female rats, J. Endocrinology, 165:569-577, 2000.*

Iannoli et al., Epidermal growth factor and human growth hormone accelerate adaptation after massive enterectomy in an additve nutrient-dependent, and site-specific fashion, Surgery, 122:721-729, 1997.*

Thompson, J.S., Epidermal growth factor and the short bowel syndrome, J. Parenteral and Enteral Nutrition, 23(5):S113-S116, Sep./Oct. 1999.*

Deghenghi et al., GH-releaseing activity of hexarelin, a new growth hormone releasing peptide, in infant and adult rats, Life Sci. 54(18):1321-1328, 1994.*

Bowers et al., On the in vitro and in vivo activity of a new synthetic hexapeptide that acts on the pituitary to specifically release growth hormone, Endocrinol. 114(5):1537-1545.*

Lecour et al., Identification of a novel role for sphingolipid signaling in TNF-alpha and ischemic preconditioning mediated cardioprotection, J. Mol. Cell. Cardiol. 34:509-518, 2002.*

Martin et al., Timing, route, and dose of administration of heparin-binding epidermal growth factor-like growth factor in protection against intestinal ischemia-reperfusion injury, J. Ped. Surg. 40:1741-1747, 2005.*

* cited by examiner

PHARMACEUTICAL COMBINATION FOR THE TREATMENT OF TISSUE DAMAGE OWING TO AN ARTERIAL IRRIGATION DEFECT

BACKGROUND OF THE INVENTION

This invention relates to a medicine for humans, and particularly to a pharmaceutical combination of Epidermal Growth Factor (EGF) and Growth Hormone secretagogue hexapeptide (GHRP) for use in preventing tissue damage due to blood flow suppression and in enhancing tissue repair following ischemic damage.

All the organs in the animal body are susceptible to lethal irreversible tissue damage following partial or full-arterial blood flow deprivation, or venous drainage failure. In these scenarios, cellular death is the aftermath of a progressive cascade of pathophysiological changes, which may eventually threaten appropriate multi-organ functioning and an individual's survival.

Exaggerated ROS generation is a key pathological consequence of a myriad of processes linked to tissue hypoperfusion, ischemia/reperfusion, and inflammation (peritonitis, pancreatitis, etc). Tissue hypoperfusion and reactive oxygen species (ROS) over-production are also associated to major surgery, revascularization surgery, extensive burns and multiple traumas. Membranes lipid peroxidation by ROS attack is responsible for cellular demise in many pathologic conditions (T. D. Lucas and I. L. Szweda. Cardiac reperfusion injury. Aging, lipid peroxidation and mitochondrial dysfunction. Proc Natl Acad Sci USA 1998, 95 (2): 510-514).

Depletion of cellular ATP stores is the most acute and threatening consequence of ischemia (Burns T A, Davies R D, McLaren J A, Cerundolo L, Morris J P, Fuggle V S. Apoptosis in ischemia/reperfusion injury of human renal allografts. Transplantation. 1998, 66 (7): 872-876). Along the ischemic process, ATP stores are degraded to hypoxantine and xantine, both acting as substrates for the enzyme xantine oxidase (XO). The large availability of incoming molecular oxygen during the reperfusion period leads to purine oxidation via XO activation, resulting in superoxide anion and hydrogen peroxide generation (Paller M S, Hoidall J R, Ferris J E. Oxygen free radicals in ischemic acute renal failure in the rat. J Clin Invest 1994, 74: 1156-1164.). During ischemia/reperfusion periods, ROS generation and microvascular failure combine to act as a vicious circle, in which activated endothelial cells and circulating leukocytes recruitment/adhesion further increase territorial tissue perfusion and thus cellular hypoxia (Redl H, Gasser H, Hallstrom S, Schlag G. Radical related cell injury. In Pathobiology of shock, sepsis and organ failure. G. Schlag, H. Redl, editors. Springer-Verlag, Heidelberg. Germany 1993, 92-110); (Ledebur H C, Parks T P. Transcriptional regulation of the intercellular adhesion molecule 1 gene by inflammatory cytokines in human endothelial cells: essential roles of a variant NF-kB site and p65 homodimers. J Biol Chem 1995, 270: 933-943).

ROS may activate NF-kB in tissues infiltrated by inflammatory cells (Conner E M, Brand S J, Davis J M, Kang D Y, Grisham M B. Role of reactive metabolites of oxygen and nitrogen in inflammatory bowel disease: toxins, mediators, and modulators of gene expression. Inflamm Bowel Dis 1996, 2: 133-147), whereas the myeloperoxidase (MPO) enzyme system is activated in polymorphonuclear cells infiltrating hypoxic tissue which further amplify the tissue damage cascade (Kurose I, Argenbright L W, Wolf R, Lianxi L, Granger DN. Ischemia/reperfusion-induced microvascular dysfunction: role of oxidants and lipid mediators. Am J Physiol 1997, 272: H2976-H2982). In this hostile environment, local thrombogenic mechanisms are activated which results in capillary plugging and hypoxia territorial expansion. As a consequence of this cascade, cellular death ensues by necrosis and/or apoptosis, which may compromise an organ's viability (Tredger M J. Ischemia-reperfusion injury of the liver: treatment in theory and practice. Biofactors 1998, 8 (1-2): 161-164). Endothelial/inflammatory cell reactivity renders a large number of chemical soluble mediators such as nitric oxide, pro-inflammatory cytokines, pro-coagulant and vasoactive agents which may trigger the Systemic Inflammatory Response Syndrome (SIRS) if the body is incapable of counteracting its immune dissonance (Kowal-Vern A, McGill V, Gamelli R L. Ischemic necrotic bowel disease in thermal injury. Archives of Surgery 1997, 132 (4): 440-443). Major burns are medical emergencies demanding intensive and multiple medical efforts to save a patient's life. In burn patients, gut hypoperfusion 1 ischemia seems to play a critical role in orchestrating the SRIS (Wang P, Ba Z F, Cioffi W G, Bland K I, and Chaudry I H. Is gut the "motor" for producing hepatocellular dysfunction after trauma and hemorrhagic shock? Journal of Surgical Research 1998, 74: 141-148). Intestinal barrier failure is of paramount clinical relevance as the gut epithelium acts as a frontier between a septic/toxic lumen and a sterile internal environment (Sheridan R L, Ryan C M, Yin L M, Hurley J, Tompkins R G. Death in the burn unit. Sterile multiple organ failure. Burns 1998, 24 (4): 307-311).

In this regard, both experimental and clinical findings converge to show the importance of an adequate intestinal perfusion during systemic stress as to preserve barrier integrity (Tabata T, de Serres S, Meyer A A. Differences in IgM synthesis to gut bacterial peptidoglycan ploysaccharide after burn injury and gut ischemia. Journal of Burn Care and Rehabilitation 1996, 17 (3): 231-236). Furthermore, recent evidences also indicate that intestinal tissue acts as a pro-inflammatory cytokine-generating source when intestinal-associated lymphoid tissue is activated by ischemia. Multiple organ failure (MOF) is a first cause of death in patients admitted under intensive care conditions, and is the most frequent complication for burn victims, involving up to a 70% of patients in highly specialized burn treatment units.

In order to attenuate the consequences of the ischemia/reperfusion process in certain organs, a large number of synthetic or natural compounds have been pre-clinically or clinically examined. For the case of intestinal ischemia, angiotensin II inhibitors were experimentally evaluated (Tadros T, Taber D L, Heggers J P, Herndon D N. Angiotensin II inhibitor DuP753 attenuates burn and endotoxin-induced gut ischemia, lipid peroxidation, mucosal permeability and bacterial translocation. Ann Surg 2000; 231: 566-576). Platelet activating factor inhibitors (Sun Z, Wang X, Deng X, Lasson A, Soltesz V, Borjesson A, Andersson R Beneficial effects of lexipafant, a PAF antagonist on gut barrier dysfunction caused by intestinal ischemia and reperfusion in rats. Dig Surg 2000; 17: 57-65), and enhancers of nitric oxide release were also studied (Ward D T, Lawson S A, Gallagher C M, Conner W C, Shea-Donohue D T. Sustained nitric oxide production via L-arginine administration ameliorates effects of intestinal ischemia-reperfusion. J Surg Res 2000; 89: 13-19). Other approaches include anti-oxidant therapy such as allopurinol alone or in combination with vitamins C and E (Kacmaz M, Otzurk H S, Karaayvaz M, Guven C, Durak I. Enzymatic antioxidant defense mechanism in rat intestinal tissue is changed after ischemia-reperfusion. Effects of allopurinol plus antioxidant combination. Can J Surg 1999; 42: 427-431).

Despite this, efforts forwarded to spark cellular natural defensive mechanisms are scarce (Pialli S B, Hinmn C E, Luquette M H, Nowicki P T, Besner G E. Heparin-binding epidermal growth factor-like growth factor protects rat intestine from ischemia/reperfusion injury. J Surg Res1999; 87: 225-231). Renal demise following ischemia/reperfusion has fueled the search for nephroprotective agents, including the generation of the so-called lazaroids, which have shown to confer global protection to the ischemic kidney (De Vecchi E, Lubalti L, Beretta C, Ferrero S, Rinaldi P, Galli K M, Trazzi R, Paroni R. Protection from renal ischemia-reperfusion injury by the 2-methylaminochroman U83836. Kidney Int 1998, 54: 857-863). Other studies document the salutary effects of teofilin in renal protection, chiefly as an antagonist to adenosine receptors (Jenik A G, Ceriani J M, Gorenstein A, Ramirez J A, Vain N, Armadans M, Ferraris J R. Randomized, double-blind, placebo-controlled trial of the effect of theophylline on renal function in term neonates with perinatal asphyxia. Pediatrics 2000; 105: E45).

Administration of the atrial natriuretic peptide (Auriculin) did not reduce mortality in patients affected by acute renal failure and remote organs complications were not reduced (Weisberg L S, Allgren R L, Genter F C, Kurnik B R. Cause of acute tubular necrosis affects its prognosis. The Auriculin Anaritide Acute Renal Failure Study Group. Arch Intern Med 1997; 157: 1833-1839). Nephroprotection has been attributed to the enzyme superoxide dismutase (SOD) when injected at high dose levels in patients undergoing renal transplant surgery (Schneeberger H, Schleibner S, Illner W D, Messmer K, Iand W. The impact of free-radical mediated reperfusion injury on acute and chronic rejection events following cadaveric renal transplantation. Clin Transpl 1993; 219-232).

The benefits of EGF and TGF-alpha in ameliorating toxic and ischemic acute renal failure are shown in U.S. Pat. No. 5,360,790. Although the parenteral administration of some growth factors exhibiting nephroprotective effects has proven effective in experimental models, so far clinical results are discouraging. A controlled multicenter clinical trial did not show the expected benefits of IGF-I in acute renal failure patients when compared to placebo counterparts (Hirschberg R, Kopple J, Lipsett P, Benjamin E, Minei J, Albertson T, Munger M, Meztler M, Zaloga G, Murray M, Lowry S, et al. Multicenter clinical trial of recombinant human insulin-like growth factor I in patients with acute renal failure. Kidney Int 1999; 55:2423-2432). In a further clinical trial employing IGF-I for acute renal failure, the lack of effect was confirmed (Kopple J D, Hirschberg R, Guler H P, Pike M, and Chiron Study Group: lack of effect of recombinant human insulin-like growth factor-1 (IGF-1) in patients with acute renal failure (ARF). J Am Soc Nephrol 1996; 7: 1375). Scarce progress in organ preservation technology achieved thus far remains the most important limitation of new organ availability for transplantation. Furthermore, ex-vivo preservation agents have yielded conflicting effects (Schlumpf-R; Candinas-D; Weber-M; Rothlin-M; Largiader-F. Preservation of kidney transplants with a modified UW solution initial clinical results. Swiss-Surg. 1995 (4): 175-80; discussion 180-1); and organ biochemical and functional deterioration following implantation into the recipient remains the first cause of non-immune rejection (Barber E, Menéndez S, León O S, Barber M O, Merino N, Calunga J L, Cruz E, and Bocci V. Prevention of renal injury after induction of ozone tolerance in rats submitted to warm ischemia. Mediators of Inflammation 1999; 8: 37-41). An untoward effect reported for some preservation agents is its interference in platelet aggregation mechanism, thus leading to profuse bleeding (Salat A, Mueller M R, Boehm D, Stangl P, Pulaki S, Laengle F. Influence of UW solution on in vitro platelet aggregability Transpl-Int. 1996; 9 Suppl 1: S429-431). Vasospasm and thrombosis in the post-reperfused organ are amongst the inconveniences reported (Jeng-LB; Lin-PJ; Yao-PC; Chen-MF; Tsai-KT; Chang-CH. Impaired endothelium-dependent relaxation of human hepatic arteries after preservation with the University of Wisconsin solution. Arch-Surg. 1997 January; 132(1): 7-12). The medical community still expects more efficient and less expensive organ preservation solutions (Rentsch M, Post S, Palma P, Gonzalez A P, Menger M D, Messmer K. Intravital studies on beneficial effects of warm Ringer's lactate rinse in liver transplantation. Transpl Int. 1996; 9(5): 461-7). The failure of IGF-I in affording an efficient nephroprotective effect in the clinical arena has introduced the notion that therapy with a single growth factor is not sufficient to stimulate cellular survival during ischemia/reperfusion, and that growth factor cocktails will be more efficacious (Playford R J. Peptides and gastrointestinal mucosa integrity. Gut 1995, 37: 595-597).

The salutary effects of Epidermal Growth Factor (EGF) in protecting organ damage during ischemia/reperfusion episodes was claimed by European patent EP 0 357 240 B1. However, cerebral protection is only achieved with very high EGF concentrations (1 mg/kg). A lower dose of 0.1 mg/kg only showed a modest protective effect despite the dose being high for a substance like a growth factor. These facts impose limitations to the invention, the first one is related to the high cost of the treatment as repeated injections (4 to 5) are required to achieve an effect in the animal. As an example, a 70-kg human subject would require 70 mg of EGF in a single injection, which will have to be periodically repeated to ensure a clinical effect. The second limitation is pharmacologic. The examples shown in the patent suggest that there is a very narrow therapeutic window that hinders the possibility of establishing an Effective Dose 50 ($ED_{50}$) and a dose-response curve. A third limitation is associated with high EGF doses. Reports exist demonstrating that in rats and monkeys, EGF may depress heart output and arterial pressure (Keiser J A, Ryan N J. Hemodynamic effect of EGF in conscious rats and monkeys. PNAS USA 1996; 93(10): 4957-4961). Normal cell cycle progression may also be perturbed by high concentrations of EGF (Bennett N T, Schultz G S. Growth factors and wound healing: Biochemical properties of growth factors and their receptors. Am J Surg 1993, 165:728-737). The potential benefits of EGF intervention in protecting the liver and the intestines against ischemia/reperfusion seem to require further elucidation. Mounting evidence indicates that the parenteral administration of EGF seem to confer protection to a variety of internal epithelial organs following acute blood flow suppression. In experimental conditions with animals exposed to a chemical, which blocks ATP synthesis or increases the rate for EROs generation, EGF intervention proved to be useful by reducing organ damage. Furthermore, repeated EGF administration assists in enhancing tissue regeneration, adaptation and functionality. All of these benefits of EGF therapy may only be achieved under repeated administration regimes and high concentrations of the polypeptide. Often, these benefits are modest, which further strengthen the notion that a combined therapy of growth factors is rather preferable. In the context of ischemia, EGF seems to attenuate tissue damage if ischemia time is less than 60 minutes. For larger ischemia periods, EGF therapy is worthless. This is an obvious limitation for EGF therapy as protection for larger ischemic periods is required in surgical practice.

Although the need of growth factor combination has been emphatically claimed for a large period of time, there is no combination available in the clinical armamentarium.

DETAILED DESCRIPTION OF THE INVENTION

The novelty of the present pharmaceutical composition is given by the pharmacological synergy set forth by the combination of Epidermal Growth Factor (EGF) and a Growth Hormone secretagogue peptide (six) (GHRP-6). This combination enhances cellular viability in organs or tissue which have undergone partial or full suppression of blood supply for a period of minutes to hours. This combination reduces or prevents EROs generation as other toxic metabolites in hypoxic or anoxic organ which stimulates cell survival during ischemic periods. The combination of these two peptides exert a potent synergistic activity in enhancing organ adaptation; i.e., intestinal adaptation following extensive trauma and the repair process.

By means of a prophylactic pre-conditioning intervention, the combination of the peptides allows for the activation of cellular self-defense mechanisms, thus increasing cellular tolerance to cytotoxic agents or stressful conditions. Thus, by cellular preconditioning this combination turns non-lethal what otherwise is lethal under ordinary conditions. This allows for the applicability of this combination to organs or organisms undergoing critical and threatening conditions as ischemia, low flow states, shock, hemodynamic failure, etc. Beside the protective effects of the combination, it enhances tissue repair, regeneration and functional adaptation following trauma. Subjects exhibiting extensive burn injuries, multiple traumas, and shock are tributary to receive the combination as soon as possible in order to attenuate the ongoing cascade of internal organ damage as to prevent or delay the onset of multiple organ failure. Subjects electing for major or prolonged surgery, extra-corporeal circulatory machine support, etc, must receive the present combination in order to ameliorate the risk of splanchnic and other internal organ damage as to attenuate the Systemic Inflammatory Response Syndrome. The combination is applicable as well to attenuate organ/tissue damage associated to thrombosis and embolism once the appropriate thrombolytic therapy is established.

Due to the synergistic effect of the peptides in relation to trophic/regenerative actions, this combination is useful to accelerate intestinal adaptation in short bowel patients. Regeneration of hepatic mass and of renal tubular system may also be stimulated by the combination.

In a preferred embodiment of this invention, a pharmaceutical composition combines in a single product EGF and GHRP-6, which exert a potent cytoprotective action on tissues and organs exposed to hypoxic or anoxic events. The combination affords cytoprotection by different mechanisms which are up regulated following a single pre-conditioning dosification. The combination may be associated to any of the standard anti-oxidant therapeutic modalities.

On the other hand, the therapeutic administration of the combination when oriented to stimulate tissue regeneration requires repeated administration. The referred EGF encompasses that of natural, synthetic or recombinant origins. The referred secretagogue peptide is the hexapeptide having the following amino acid sequence: His-D-Trp-Ala-Trp-D-Phe-Lys-NH$_2$. It is referred to as GHRG-6 (Growth Hormone Releasing Peptide).

The combination also refers to the independent administration of both peptides to a single individual within a single therapeutic scheme.

When the combination is prophylactically applied to prevent ischemic tissue damage, the EGF concentration in the pharmaceutical combination is between 0.5 and 50 µg/ml irrespective to its presentation as a lyophilized salt or as a solution. GHRP-6 concentration may range from 2-100 µg/ml in the same vehicle. Dose ranges of 0.5 and 1 µg/kg are recommended for both EGF and GHRP-6 for prophylactic goals.

The combination must be administered as a bolus. Administration routes may involve peripheral or deep veins, intra-arterial and or/intraperitoneal. Vehicles to be used for administrations include: normal saline solution, lactated Ringer solution, human plasma, human albumin solution, 5% dextrose, and mixtures thereof.

In order to ensure the highest efficacy of the therapy, the first administration should be made as soon as possible after ischemia is diagnosed or suspected or when it will be surgically created. For patients bearing extensive burns, multiple traumas, shock, etc, the treatment should be initiated despite the absence of any clinical or complementary indication of splanchnic ischemia as a prophylactic intervention. Patients bearing non-septic pancreatitis also benefit from treatment under the above specifications.

The prophylactic administration schedule may fluctuate according to the severity of the clinical picture and/or the magnitude of the aggression, which are at the discretion of a professional skilled in the art. Bolus administration can be repeated every 6 hours as to complete four administrations per day. It is necessary to maintain a lag period of 6 hours between each application. The combination of peptides can be administered using slow release technology devices. The combination of the products, if lyophilized, must be resuspended prior to use.

As previously described when the combination is for therapeutic goals, which means that its use is aimed to stimulate regeneration and adaptation, treatments must be preferably administered via slow release systems or through alternative means as to ensure a bi-compartmental equilibrium of phases. Bolus infusions are not effective in stimulating tissue regeneration. If venous lines are used, administration period must be calibrated to last for about 4 hours. More than two administrations in a 24 hour period can be carried out if a clearance period of at least 8 hours is between the treatments. Recommended doses of both peptides for regeneration are 0.01 µg/kg/h up to 5 µg/kg/h. These administration and dosing regimes allow the restoration of tissue damaged by ischemia in which necrosis and or/apoptosis are involved. When tissues are exposed to brief ischemia periods, administering the combination interrupts further complications. The use of the combination is recommended following transplantation surgery as to enhance anastomotic healing, tissue regeneration, and re-adaptation of the implanted organ. Repeated administrations of the combination also recommended to treat the short bowel syndrome and the acute intestinal failure following large intestinal surgery.

EXAMPLES

Example 1

Cytoprotective Effect of the GH Secretagogue Hexapaptide (GHRP6) in an Animal Model of Acute Gastric Stress Damage

Adult, male OF-1 mice (20-23 g) were randomly assigned to receive GHRP-6 (0.1 μg/animal) or normal saline solution 0.9% (both i.p.). Ten to thirty minutes later animals were forced to swim in cold water for 30 minutes and later restrained for another 20 minute period at 4° C. Animals were thereafter anesthetized and euthanized for gastric mucosa inspection. Samples were fixed in 10% buffered formalin and H&E, and PAS stained for microscopic examination. Erosion, hemorrhage, and ulceration were the gross pathology criteria considered in the experiment (Playford RJ. Peptides and gastrointestinal mucosa integrity. Gut 1995, 37: 595-597). Microscopic ulceration was only considered when deeper than the first third of the glandular mucosa. Luminal bleeding was studied by measuring hemoglobin by the cyano metahemoglobin method (Reactivos Spinreact, Barcelona). Data were expressed in g/dL. All determinations were done in a blind fashion using a sham group.

As shown in table 1, GHRP-6 significantly reduced the intensity of mucosal damage as seen by the number of ulcers on the oxyntic mucosa.

TABLE 1

Gastroprotective effect of the systemically administered GHRP-6

| Damage | Controls (Saline 0.9%) | GHRP-6 |
|---|---|---|
| Epithelial Erosion | 20 (100%) | 6 (30%)* |
| Mucosal Hemorrhage | 16 (80%) | 0 (0%)* |
| Luminal Hemorrhage | 12 (60%) | 0 (0%)* |
| Luminal Hemoglobin | 4.3 | 0* |
| Total of ulcers | 68 | 3* |

A total of 20 mice were used for each group. * $p<0.01$ established for two-tailed t-test. Significance level of $p<0.05$.

This experiment demonstrates the cytoprotective effect of the GHRP-6, expressed on the gastric mucosa of animals exposed to a severe systemic stress. Gastric mucosa ischemia/reperfusion has been implicated in the pathophysiology of this acute damage model.

Example 2

Protective Effect of the Prophylactic Administration of EGF and GHRP-6 in an Animal Model of Renal Ischemia/Reperfusion

Experimental Design

The potential nephroprotective effects of each of the peptides alone or in combination was studied in a rat model of renal bilateral ischemia/reperfusion. In a first phase trial, a ischemia period of 1 hour followed by a 3 hour reperfusion period was established. Female Wistar rats (200-220 g) were randomly assigned to the following experimental groups (N=10):

Group I: Sham ischemic.
Group II: Ischemic and normal saline solution 0.9%.
Group III: Ischemic and EGF –20 μg/rat.
Group IV: Ischemic and GHRP –6-50 μg/rat.
Group V: Combination between EGF (5 μg) y GHRP-6 (10 μg).

All the treatments were intraperitoneally administered 30 minutes before ischemia.

Ischemia Model

Renal arteries were clamped with microvascular clamps (Moria, Fine Science Tools, USA) for 60 minutes. After 3 hours of reperfusion the animals were monitored for another 30 minutes to establish renal functioning.

Renal Functioning

Glomerular filtration rate (GFR) and the renal plasmatic flow (RPF) were studied using molecular weight markers as inulin and p-amino hypuric. Clearance coefficients were determined as follows:

$C = Uv(m) \times [PM]u/[PM]p$

Uv(m) maximal urine volume per minute.
[PM]u and [PM]p represents plasma and urine concentrations of each marker Data are expressed as ml/min/g of weight.

Diuresis Volume

A catheter was fixed in the urinary bladder and the urethra was clamped. The free end of the catheter was inserted in a graduated tube and the urine volume was collected during 10 minutes.

Biochemical Determinations

Renal tissue samples were homogenized in KCl/histidine (pH7.3) buffer and the supernatant was used to measure the activity of the enzymes PLA2, catalase, as the MDA reactive metabolite.

Histological Determinations

Renal tissue samples were fixed in 10% buffered formalin, paraffin embedded, H&E stained and studied by independent pathologists using the following criteria: number of collapsed glomeruli, cortical hemorrhage, medullar hemorrhage, severe tubular damage, and severe interstitial damage. As shown in table 2, ischemia/reperfusion event provoked a marked deterioration of the renal urine formation capacity. EGF intervention attenuated the oliguria with respect to saline-treated controls. GHRP-6 intervention increased urine formation 4 times as compared to saline treated animals, which argues in favor of renal functional protection. EGF/GHRP-6 combined administration completely prevented renal failure so that diuresis was similar to a non-ischemic reference group. These data confirm the synergistic effect of the present peptide combination.

TABLE 2

Urine output during the reperfusion period.

| Sham | Ischemia/ saline 0.9% | Ischemia/ EGF (20 μg) | Ischemia/ GHRP (50 μg) | Combination |
|---|---|---|---|---|
| 311 ± 14** | 51 ± 40 | 114 ± 51 | 208 ± 47* | 382 ± 19** |

Data expressed as mean and SD.
**Mean difference $p < 0.05$ in relation to ischaemic animals receiving saline 0.9%.
*Mean difference $p < 0.05$ in relation to ischaemic animals receiving saline 0.9%. Mann Whitney-U test.

The microscopic examination showed that ischemia affected the three main structures of the kidney: glomeruli, tubular apparatus, and the interstitial tissue. Damage was severe in animals receiving saline. Both EGF and GHRP-6 conferred renal protection to the animals assigned to each independent treatment. In general and qualitative terms GHRP-6 seems to afford larger protection to the renal parenchyma than EGF alone. The combination of both peptides is steadily better in comparison to each agent alone. Data are shown in table 3.

TABLE 3

Percent of animals/group showing renal tissue damage.

| Groups | Damaged Glomeruli | Cortical Hemorrhage | Medullar Hemorrhage | Tubular Damage | Interstitial Damage |
|---|---|---|---|---|---|
| Sham | 0 | 0 | 0 | 0 | 0 |
| Ischemia/saline | 100 | 97 | 100 | 100 | 98 |
| Ischemia/EGF | 59♠ | 68♠ | 63♠ | 53♠ | 75♠ |
| Ischemia/GHRP-6 | 49♠ | 17♠ | 25♠ | 25♠ | 22♠ |
| Combination | 5**♣ | 0**♣ | 2**♣ | 0**♣ | 0**♣ |

**Mean difference (p < 0.01) with the ischaemic groups receiving saline.
♠Mean difference (p < 0.05) with the ischaemic groups receiving saline.
♣Mean difference p < 0.01 between groups receiving EGF and GHRP-6 as compared to the group treated with the peptide combination. Comparisons made by one-way ANOVA and Duncan's multiple range test.

Histopathology data were confirmed by renal functional tests given by the clearance of both plasmatic markers. EGF and GHRP-6 partially attenuate renal failure when given independently. The combination again, has proved to confer total renal protection. These data are shown in table 4.

TABLE 4

Renal function.

| Groups | Renal Plasmatic Flow (ml/min/100 g) | Glomerular Filtration Rate (ml/min/100 g) |
|---|---|---|
| Sham | 2.53 ± 0.4 | 0.71 ± 0.12 |
| Ischemia/saline | 0.66 ± 0.2 | 0.22 ± 0.11 |
| Ischemia/EGF | 1.2 ± 0.61 | 0.3 ± 0.15 |
| Ischemia/GHRP-6 | 1.88 ± 0.8# | 0.46 ± 0.23# |
| Combination | 2.67 ± 0.66*♣ | 0.73 ± 0.1*♣ |

*Difference between the group treated with the peptide combination and the one receiving normal saline solution (p < 0.01).
♣Difference between the group treated with the peptide combination and those receiving each peptide alone (p < 0.05).
p < 0.05 between the group receiving GHRP-6 and the one receiving saline solution. Comparisons made by one-way ANOVA and Duncan's multiple range test.

During a second phase study, a larger ischemia period was introduced which allowed for studying the effect of the peptide in a more practical model with respect to the clinical practice. Kidneys were exposed to a 3 hours ischemia period and a similar reperfusion time. As demonstrated in table 5 following 3 hours of ischemia period, overt renal failure is noted. Urine volume collected from animals receiving saline and EGF is negligible and contains hemoglobin. Partial nephroprotection is detectable in animals treated with GHRP-6, so that diuresis is significantly higher than that seen in saline and EGF groups. It was lower than that detected for the reference non-ischemic group. The EGF/GHRP-6 combination provided nephroprotection as judged by the similarity of diuresis values with the non-ischemic reference group.

TABLE 5

Urine out put during the reperfusion period.

| Sham ischaemic | Ischemia/saline 0.9% | Ischemia/EGF (20 µg) | Ischemia/GHRP (50 µg) | Combination |
|---|---|---|---|---|
| 395 ± 43 | 28 ± 10 | 83 ± 21 | 168 ± 33* | 282 ± 32♣# |

Data expressed as mean and SD.
*Difference (p < 0.05) between the GHRP-6 group and that receiving normal saline.
♣Difference between the group treated with the peptide combination, EGF-treated and the ischaemic control receiving saline (p < 0.01).
p < 0.05 between the group receiving GHRP-6 and the one receiving saline solution. Comparisons made by one-way ANOVA and Duncan's multiple range test.

From a histopathological point of view, the renal damage was massive and severe in most of the animals. Protection in qualitative terms was detected as follows: Peptide Combination/GHRP-6/EGF. As seen from the animals receiving the peptide combination, protection by EGF and GHRP-6 was negligible when independently given. Data is shown in table 6 demonstrating the protection conferred by the peptide combination.

TABLE 6

Percent of animals/group showing renal tissue damage.

| Groups | Damaged Glomeruli | Cortical Hemorrhage | Medullar Hemorrhage | Tubular Damage | Interstitial Damage |
|---|---|---|---|---|---|
| Sham ischaemic | 0 | 0 | 0 | 0 | 0 |
| Ischemia/saline | 100 | 100 | 100 | 100 | 90 |
| Ischemia/EGF | 80 | 70 | 80 | 90 | 80 |
| Ischemia/GHRP-6 | 60♦ | 40♦ | 80 | 50♦ | 30♦ |
| Combination | 10♣ | 0♣ | 10♣ | 10♣ | 0♣ |

♦Difference between the group treated with GHRP-6 and the ischaemic control group receiving saline solution (p < 0.05).
♣Mean difference between the group receiving the peptide combination and the rest of the groups under ischemia irrespective to the treatment (p < 0.05/p < 0.01). Significance level for p < 0.05. Comparisons by one-way ANOVA and Duncan multiple range test.

Renal functional analysis showed again that the peptide combination ensured appropriate rates of glomerular blood flow and tubular filtration. Even under the present ischemia conditions these functional markers were within normal ranges as detected in the sham ischemic animals. Data are shown in table 7.

TABLE 7

Renal function

| Groups | Renal Plasmatic Flow (ml/min/100 g) | Glomerular Filtration Rate (ml/min/100 g) |
|---|---|---|
| Sham | 2.75 ± 0.7 | 0.82 ± 0.1 |
| Ischemia/saline | 0.02 ± 0.01 | 0 |
| Ischemia/EGF | 0.6 ± 0.05 | 0.24 ± 0.15 |
| Ischemia/GHRP-6 | 1.07 ± 0.8♣ | 0.38 ± 0.2♣ |
| Combination | 2.15 ± 0.36* | 0.78 ± 0.01* |

*Difference between the group receiving the combination and the rest of the ischaemic groups ($p < 0.01$).
♣Difference between the group treated with GHRP-6 and the saline treated group 0.9% ($p < 0.05$). Significance level for $p < 0.05$. Comparisons by one-way ANOVA and Duncan multiple range tests.

This study has confirmed the superiority of the peptide combination in preventing renal structural damage and functional demise by prolonged ischemia/reperfusion periods.

Example 3

Protective Effect of the EGF/GHRP-6 Combination in an Intestinal Ischemia/Reperfusion Model Male Sprague Dawley (220-250 g) rats were randomly assigned to the following treatment groups:
I: ischemia/normal saline.
II: Ischemia EGF 500 μg/rat.
III: Ischemia/GHRP-6 100 μg/rat.
IV: Ischemia/combination -EGF (5 μg)/GHRP-6 (2 μg)/rat.
All the treatments were intraperitoneally administered 30 minutes prior to beginning the ischemia period.
Experimental Model Under methoxyfluorane anesthesia and thermal blanket, a careful laparatomy was performed to expose the first order branch of the mesenteric superior artery. The artery was clamped for a period of 2 hours, thus provoking a severe ischemia time on the jejunum and ileum portions of the small intestine. Reperfusion was allowed for 3 hours. Rats were euthanized and subjected to complete autopsy. The small intestine was resected and the length of hemorrhagic mucosal and/or luminal damage was registered. Luminal content was flushed out with a standard volume of saline to determine the hemoglobin content. Intestinal mucosa was washed with warm normal saline, weighed and fragments used to determine total protein content by Lowry method. Other fragments were used for total DNA content and microscopic analysis. Villi/mucosal damage was microscopically analyzed as described by Chiu. This scale considers Grade 0 as intact mucosa progressing to Grade 5 as full-thickness denudation.

In order to fully elucidate the protective effect of the combination treatment in this model of intestinal ischemia/reperfusion, survival was monitored until 96 hours of reperfusion.

Animals receiving normal saline were seriously affected by the ischemia/reperfusion period used here, exhibiting a transmural ulcer with total denudation and profuse bleeding. As shown in table 8, most of the intestinal segments studied in this group exhibited a grade 5-damage pattern. EGF treatment conferred a minimal protection, which in the clinical practice seems irrelevant. EGF intervention provided a minimal effect. A partial protection was evidenced in animals receiving the GHRP-6 so that mucosal damage was more superficial and more circumscribed. Again, the peptide combination significantly reduced mucosal damage (table 8). All the criteria used in the study confirm that the peptide combination confers a remarkable cytoprotective effect along the ischemia/reperfusion event.

TABLE 8

Intestinal damage parameters.

| Experimental Groups | % of intestinal damage | Mucosal Weight (g) | Proteins Content (mg/cm) | Luminal hemoglobin (g/dL) | DMA content (μg/cm) | Damage Index (0-5) |
|---|---|---|---|---|---|---|
| Ischemiasaline | 96.3 ± 1.1 | 8.53 ± 2.18 | 0.72 ± 0.4 | 6.44 ± 1.37 | 0.25 ± 0.13 | 5 |
| EGF-500 μg | 78.7 ± 2.8 | 10.7 ± 4.5 | 1.08 ± 0.6 | 3.5 ± 1.02 | 0.4 ± 0.11 | 4.2 |
| GHRP-6-100 μg | 63 ± 14.5♣ | 11.3 ± 1.6♣ | 1.88 ± 0.75♣ | 1.23 ± 0.82♣ | 0.58 ± 0.24♣ | 3.88♣ |
| Combination EGF + GHRP-6 | 11.5 ± 6.4* | 14.5 ± 1.2* | 2.85 ± 0.66* | 0* | 0.79 ± 0.03* | 1.27* |

Data expressed as mean value and SD.
*Mean difference between the group receiving the peptide combination and the ischaemic group receiving saline solution ($p < 0.01$).
♣Means difference between the group receiving the GHRP-6 and the saline treated group ($p < 0.05$). Comparisons by one-way ANOVA and Duncan multiple range test.

Microscopic examination of the main internal organs demonstrated a close correspondence between the magnitude of the intestinal damage and the extra intestinal changes found in remote organs. The principal damage found attenuated in animals treated with the combination were: (I) neutrophilic infiltration in lungs parenchyma, (II) prevention of hepatocyte oncosis and (III) prevention of glomerular tuft collapse and tubular changes.

A second and independent experiment was conducted in order to learn if the combination stimulated animals' survival. Experimental methodology is as described above. All the rats received an intraperitoneal injection of lactated Ringer following wound closure. Animals were monitored for 96 hours once reperfusion was initiated. 100% of the rats receiving the peptide combination survived 96 hours and beyond. (Table 9).

TABLE 9

Survival per group.

| Experimental Groups (N = 10) | Survival (%) |
|---|---|
| Ischemia/saline | 0 |
| EGF (500 µg) | 20 |
| GHRP-6 (100 µg) | 40 |
| EGF (5 µg) + GHRP-6 (2 µg) | 100 |

The pathology study of these animals confirmed previous findings in that the peptide combination not only afforded a steady intestinal protection by reducing the onset of necrotic changes. Furthermore, damages damage in the lungs and kidneys as remote target organs affected by neutrophilic recruitment was also attenuated. These findings confirm the systemic and multi-organic protection triggered by the EGF/GHRP-6 combination.

Example 4

Effect of the Therapeutic Administration of the EGF/GHRP-6 in an Experimental Model of Multiple Organ Damage by Extensive Burns The dorsal region of Balb/c mice (22-25 g) was depilated and subjected to hypodermic scalding involving a 25% of body surface area, by immersion in equilibrated water at 95-97° C. for 5 seconds. All the mice received 1.5 ml of normal saline solution as fluid resuscitation immediately after. This animal model had been previously established and calibrated in our laboratory, and is useful to our goals as extensive internal changes are steadily reproduced. On the next 24 hours the surviving mice were randomly assigned to the following groups:

Reference. Sham burned mice receiving saline 0.9% (N=5).

Scalded receiving only normal saline 0.9%. (N=7)

Scalded and treated with EGF (N=10; 0.1 µg EGF/animal).

Scalded and treated with GHRP-6 (N=9; 0.1 µg GHRP-6/animal).

Scalded, treated with the peptide combination (N=10). EGF (0.01 µg) and GHRP-6 (0.01 µg).

Administrations were done twice a day and until day 10 post-scalding. Once the treatments were completed, animals were weighed again and euthanized for necropsy and microscopic examination. Six hours prior to death, every mouse received an injection of vincristine (1 mg/kg) to arrest cells on metaphase. Intestines were resected, flushed and weighed. Fragments were collected for total DNA and protein content. Other fragments were formalin fixed and used for routine processing or intestinal microdissection of villi and crypts. Morphometric procedures on the microscopic slides were derived from the DIGIPAT image processing system.

The following parameters were considered in this study:
Animal weight.
Intestinal weight, protein and DNA content.
Number of cells in metaphase per crypt.
Number of branching crypts.
Villous height.
Crypts depth.

All the mice receiving EGF, GHRP-6 alone or in combination showed a significant body weight increase at the end of the experiment. The difference was even larger in those animals receiving both peptides. These data are shown in table 10. This finding indicates the trophic effect exerted by the combination on the intestinal mucosa.

TABLE 10

Body weight along the experiment.

| Groups | Initial weight | Final weight | % Increase |
|---|---|---|---|
| Scald-saline 0.9% | 23.8 ± 1.2 | 25.3 ± 3.6 | 6 |
| Scald-EGF (0.01 µg) | 22.1 ± 2.2 | 28.2 ± 3.3* | 27 |
| Scald-GHRP (0.01 µg) | 23.3 ± 1.6 | 28.4 ± 1.8* | 23 |
| Scald-Combination EGF + GHRP-6 | 23.5 ± 1.7 | 31.7 ± 4.0*# | 34 |

Final weights were registered on the 10th day following scalding and after 20 admisistrations were completed. Data are expressed as mean and SD.
*Mean difference between the intitial and final body weight $p < 0.05$.
Difference between the group receiving the combination and the rest of the groups. One way ANOVA and Duncan.

As shown in table 11 each individual peptide treatment exerted a trophic/regenerative effect on the intestinal mucosa as compared to saline treatment. The most important effects are found in the group receiving the peptide combination.

TABLE 11

Intestinal regenerative response.

| Groups | Intestinal weight (g) | Total Protein (mg/cm) | Total DMA (µg/cm) |
|---|---|---|---|
| Intact Reference | 1.53 ± 0.25 | 2.6 ± 0.81 | 0.66 ± 0.05 |
| Scald-saline 0.9% | 0.84 ± 0.16 | 1.04 ± 0.62 | 0.41 ± 0.11 |
| Scald-EGF (0.01 µg) | 1.49 ± 0.21♣ | 2.22 ± 0.48♣ | 0.61 ± 0.08♣ |
| Scald-GHRP (0.01 µg) | 1.33 ± 0.15♣ | 2.05 ± 0.33♣ | 0.59 ± 0.01♣ |
| Scald-Combination EGF + GHRP-6 | 1.96 ± 0.1* | 3.04 ± 0.2* | 0.88 ± 0.03* |

Data are expressed as mean and SD.
*Mean difference between the group receiving the peptides combination and the saline treated one ($p < 0.01$).
♣Mean difference between groups receiving each peptide alone and the saline group ($p < 0.05$). One way ANOVA and post-Duncan test.

The most relevant evidence of this experiment is the demonstration that the peptide combination accelerates intestinal growth and adaptation given by the stimulation of the crypt fission process along the small intestine and the colon. The crypt is the growth and proliferative unit of the intestinal mucous and is as well the morphological substantiation of intestinal mass adaptation. Table 12 shows the data referring the morphological reconstitution of the intestines. Villi and crypts enlargement are in correspondence with tissue regeneration and nutrient absorption.

TABLE 12

Intestinal-mucosa restitution.

| Groups | No. of metaphases per crypt (×200) | No. of crypts in fission (×200) | Villous height (μm) | Crypts depth (μm) |
|---|---|---|---|---|
| Scald-saline 0.9% | 41 ± 16 | 12 ± 10 | 96.3 ± 26 | 33.6 ± 7 |
| Scald-EGF (0.01 μg) | 101 ± 35♥ | 25 ± 8 | 118.7 ± 19♥ | 48 ± 9 |
| Scald-GHRP (0.01 μg) | 59 ± 12 | 19 ± 6 | 99.2 ± 10 | 40.8 ± 13 |
| Scald-Combination EGF + GHRP-6 | 168 ± 22* | 77 ± 18* | 215 ± 21* | 67.5 ± 7* |

Data are expressed as mean and SD.
*Mean difference between the group receiving the peptide combination and the rest of the (p < 0.05).
♥Mean difference between the EGF group and the one receiving saline 0.9% (p < 0.05). One way ANOVA and Duncan tests.

The present invention has the following advantages:

1. The combination may exert prophylactic and/or therapeutic effects, which may depend on the requisites to be met of the pathologic condition to be treated. The effects are easily modulated by the administration regime by a professional skilled in the art.

2. The method to induce cellular protection is based on the stimulation of the self-defensive mechanism in every cell of the body. The mechanisms to be activated are different but functionally redundant. Many previous solutions for cell protection introduce foreign chemical structures (xenobiotic).

3. Small doses are enough to induce the expected therapeutic response with no risk of toxicity. Peptides have proved to be safe at very high doses in different mammals' species. Previous interventions require higher doses for modest effect.

4. Biological response is quickly activated upon the interaction of both EGF and GHRP-6 to a specific cell receptor. This precludes the need of prolonged exposures to the peptides, reducing toxic risks.

5. The peptide combination does not have contraindications and may be used in any subject with no risk. No unwanted drug interaction may occur.

6. The method is to be used for a very wide range of common clinical conditions and comorbidity, many of them with no available therapeutic choice so far.

7. The method is indicated for a number of pathology conditions including those patients undergoing transplant surgery 8. The cytoprotective effects of the present invention have a wide therapeutic window in terms of protection time against ischemia/reperfusion. Protection time meets the current clinical needs for transplantation, re-vascularization, diagnostic maneuvers, management procedures, etc.

9. From the mechanistic point of view the combination may counteract the ischemia/reperfusion damage cascade in different critical points, which turns its pharmacologic mechanisms as polyvalent and thus efficacious.

10. The use of the present combination is unique as a trophic/regenerative agent for many epithelial organs as the gut, liver, pancreas and kidney.

11. The present combination has proved to be useful for short bowel syndrome correction/intestinal adaptation. This process does not have any alternative choice in the current clinical practice.

What is claimed is:

1. A kit comprising
   (i) a first container, comprising 0.5-50 μg/ml of a peptide selected from the group consisting of epidermal growth factor (EGF), transforming growth factor type alpha (TGF-α), or heparin binding EGF-like growth factor (HB-EGF); and
   (ii) a second container, comprising 2-100 μg/ml of growth hormone secretagogue hexapeptide (GHRP-6).

2. A pharmaceutical composition comprising
   (i) 0.5-50 μg/ml of a peptide selected from the group consisting of epidermal growth factor (EGF), transforming growth factor type alpha (TGF-α), or heparin binding EGF-like growth factor (HB-EGF); and
   (ii) 2-100 μg/ml of growth hormone secretagogue hexapeptide GHRP-6.

3. A method for preventing tissue damage in a tissue or organ affected by total ischemia with no reflow, low flow states, or ischemia/reperfusion in a human or animal, the method comprising administering to the human or animal,
   (i) a peptide selected from the group consisting of epidermal growth factor (EGF), transforming growth factor type alpha (TGF-α), or heparin binding EGF-like growth factor (HB-EGF) in a dose of 0.5-1 μg per kg; and
   (ii) growth hormone secretagogue hexapeptide GHRP-6 in a dose of 0.5-1 μg per kg.

4. A method according to claim 3, wherein a combination of the peptide and the GHRP-6 is parenterally administered as a bolus.

5. A method for treating tissue damage in a tissue or organ affected by total ischemia with no reflow, low flow states, or ischemia/reperfusion in a human or animal, the method comprising administering to the human or animal,
   (i) a peptide selected from the group consisting of epidermal growth factor (EGF), transforming growth factor type alpha (TGF-α), or heparin binding EGF-like growth factor (HB-EGF) in a dose of 0.01 μg/kg/h up to 5 μg/kg/h; and
   (ii) growth hormone secretagogue hexapeptide GHRP-6 in a dose of 0.01 μg/kg/h up to 5 μg/kg/h.

6. A method according to claim 5, wherein a combination of the peptide and GHRP-6 is administered as a continuous infusion.

7. A method for preventing tissue damage in a tissue or organ affected by total ischemia with no reflow, low flow states, or ischemia/reperfusion in a human or animal, the method comprising administering to the human or animal growth hormone secretagogue hexapeptide GHRP-6 in a dose of 0.5-455 μg/kg.

* * * * *

UNITED STATES PATENT AND TRADEMARK OFFICE
CERTIFICATE OF CORRECTION

PATENT NO. : 7,361,638 B2
APPLICATION NO. : 10/220750
DATED : April 22, 2008
INVENTOR(S) : Jorge Berlanga Acosta et al.

It is certified that error appears in the above-identified patent and that said Letters Patent is hereby corrected as shown below:

IN THE SPECIFICATION:

In Column 2, Line 20,      now reads "hypoperfusion 1 ischemia"
should read --hypoperfusion/ischemia--

In Column 8, Line 54,      now reads "mean difference $p < 0.05$ in relation to ischaemic,"
should read --mean difference $p < 0.01$ in relation to ischemic,--

In Column 8, Line 56,      now reads "in relation to ischaemic"
should read --in relation to ischemic--

In Column 9, Line 12,      now reads "with ischaemic"
should read --with ischemic--

In Column 9, Line 13,      now reads "with the ischaemic"
should read --with the ischemic--

In Column 10, Line 38,      now reads "and the ischaemic;"
should read --and the ischemic--

In Column 10, Line 40,      now reads "#$p < 0.05$ between the group receiving GHRP-6 and the one receiving saline solution"
should read --Difference between the group receiving the combination as compared to the GHRP-6 group alone--

UNITED STATES PATENT AND TRADEMARK OFFICE
CERTIFICATE OF CORRECTION

PATENT NO. : 7,361,638 B2
APPLICATION NO. : 10/220750
DATED : April 22, 2008
INVENTOR(S) : Jorge Berlanga Acosta et al.

It is certified that error appears in the above-identified patent and that said Letters Patent is hereby corrected as shown below:

In Column 10, Table 6,   now reads "and the ischaemic"
                         should read --and the ischemic--

In Column 11, Line 20,   now reads "the rest of the ischaemic groups"
                         should read --the rest of the ischemic groups--

In Column 12, Line 60,   now reads "and the ischaemic group"
                         should read --and the ischemic group--

Signed and Sealed this

Eighteenth Day of November, 2008

JON W. DUDAS
*Director of the United States Patent and Trademark Office*